United States Patent [19]

Warren

[11] Patent Number: 4,606,864
[45] Date of Patent: Aug. 19, 1986

[54] THIOPHENYL THIOACRYLATE AND THIOMETHACRYLATE MONOMERS

[75] Inventor: David P. Warren, Rochester, N.Y.

[73] Assignee: Eastman Kodak Company, Rochester, N.Y.

[21] Appl. No.: 697,554

[22] Filed: Feb. 1, 1985

[51] Int. Cl.$^4$ .............................................. C07C 153/11
[52] U.S. Cl. ................................... 558/257; 556/113; 526/289; 568/57
[58] Field of Search .................................. 260/455 R

[56] References Cited

FOREIGN PATENT DOCUMENTS 2093834 2/1982 United Kingdom .

OTHER PUBLICATIONS

Testaferri et al., "Reactions of Polychlorobenzenes with Alkanethiol Anions in HMPA. A Simple, High-Yield Synthesis of Poly(alkylthio)benzenes", *J. Org. Chem.* 1980, 45, pp. 4376-4380.

*Primary Examiner*—Christopher A. Henderson

*Attorney, Agent, or Firm*—William J. Davis

[57] ABSTRACT

A monomer having the formula:

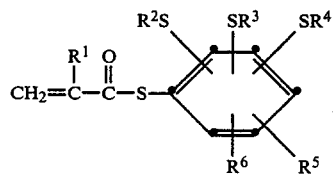

wherein:
  $R^1$ is H or methyl;
  $R^2$, $R^3$ and $R^4$ are independently alkyl, aryl, or aralkyl; and
  $R^5$ and $R^6$ are independently H, halo, alkyl, aryl, aralkyl, thioalkyl, thioaryl, or thioaralkyl, is useful in preparing a polymer having a high refractive index. The polymer is useful in forming optical components, such as lenses.

14 Claims, No Drawings

THIOPHENYL THIOACRYLATE AND THIOMETHACRYLATE MONOMERS

BACKGROUND OF THE INVENTION

1. Field of the Invention

This invention relates to novel thiophenyl thioacrylate and thiophenyl thiomethacrylate monomers, polymers thereof, and optical components containing these polymers. This invention further relates to a process for preparing these and similar monomers and to novel intermediates useful in this process.

2. Description Relative to the Prior Art

Optical components, such as lenses, prisms, and light guides are known in the art. Materials used for making optical components preferably are colorless and transparent. It is also desirable that these materials have a high refractive index. In the case of lenses, the use of high refractive index materials makes possible the use of thinner lenses having the same focal length as thicker lenses made of materials with a lower refractive index. The use of thinner lenses decreases the volume of space required by the lens within an optical assembly. The manufacture of thinner lenses requires less material, which constitutes a potential savings to the manufacturer. High refractive index materials have also been shown to be desirable in light guides as noted in U.S. Pat. No. 3,809,686.

U.K. Patent Application GB No. 2,093,834 A discloses photopolymerizable thioacrylate monomers useful in preparing polymers and copolymers having a refractive index greater than 1.6. The use of polymers having a substantially higher refractive index (over 1.7) in optical components would make possible the use of optical components which are considerably thinner than conventionally prepared components. It is thus seen that substantially transparent polymers of high refractive indices are desirable for use in optical components.

SUMMARY OF THE INVENTION

Polymers having a high refractive index (greater than 1.7) are prepared by photopolymerizing a monomer having the formula:

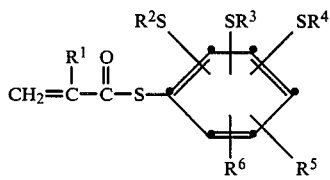

wherein:
$R^1$ is H or methyl;
$R^2$, $R^3$ and $R^4$ are independently alkyl, aryl, or aralkyl; and
$R^5$ and $R^6$ are independently H, halo, alkyl, aryl, aralkyl, thioalkyl, thioaryl, or thioaralkyl.

The resulting polymer comprises from 5 to 100 percent of the above monomer and from 0 to 95 percent of at least one copolymerizable ethylenically unsaturated monomer.

Another embodiment of the invention relates to a method of preparing an acrylate comprising (a) reacting a mercaptan with cuprous oxide to form a copper mercaptan and (b) reacting said copper mercaptan with acryloyl or methacryloyl chloride.

A further embodiment of the invention relates to a composition of matter having the formula:

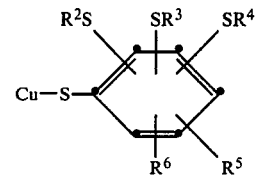

wherein $R^2$, $R^3$, $R^4$, $R^5$ and $R^6$ are as defined above which is useful in the above-described method.

DETAILED DESCRIPTION OF PREFERRED EMBODIMENTS

The novel monomer is represented by the formula:

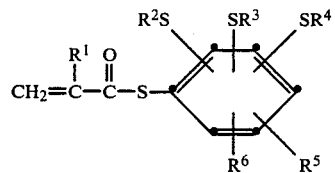

wherein:
$R^1$ is H or methyl;
$R^2$, $R^3$ and $R^4$ are independently alkyl, preferably containing 1 to about 20 carbon atoms, such as methyl, ethyl, propyl, butyl, pentyl, hexyl and the like and isomers thereof such as isopropyl, isobutyl, t-butyl and the like, most preferably containing from 1 to 6 carbon atoms; aryl, preferably containing 6 to 18 carbon atoms such as phenyl and naphthyl; or aralkyl, such as benzyl;
$R^5$ and $R^6$ are independently H; halo, such as chloro or bromo; alkyl as described for $R^2$; aralkyl such as benzyl, thioalkyl, the alkyl portion preferably containing from 1 to about 20 carbon atoms, most preferably 1 to 6 carbon atoms such as thiomethyl, thioethyl, thiopropyl, thioisopropyl and the like; thioaryl such as thiophenyl; or thioaralkyl such as thiobenzyl. Most preferably $R^5$ and $R^6$ are thioalkyl, thioaryl or thioaralkyl.

It is noted that throughout the specification and claims the terms "alkyl," "aryl," "thioalkyl," and "thioaryl" include substituted alkyl and aryl such as methoxyethyl, chlorophenyl, and bromonaphthyl.

Examples of monomers useful herein include:

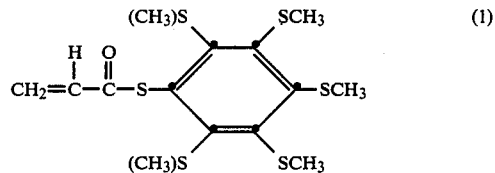

(1)

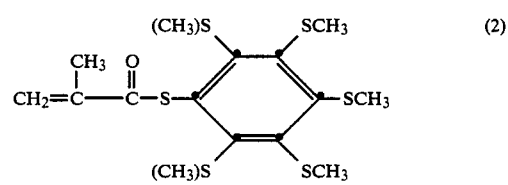

(2)

-continued

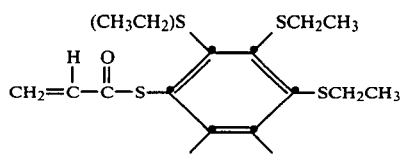 (3)

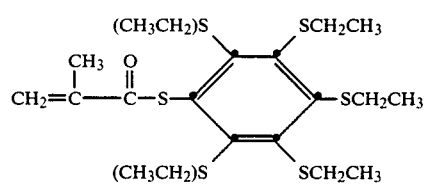 (4)

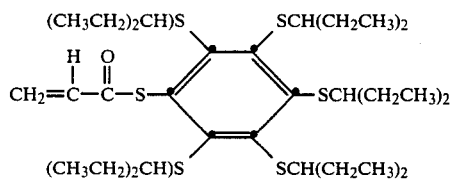 (5)

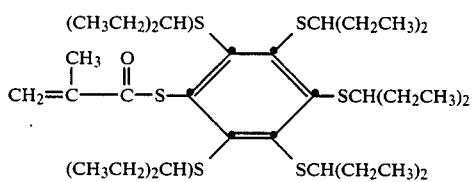 (6)

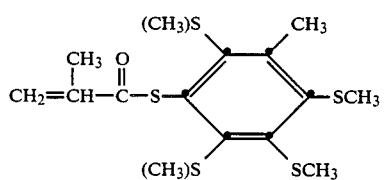 (7)

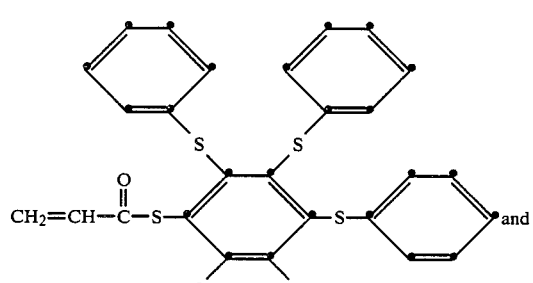 (8)

and

-continued

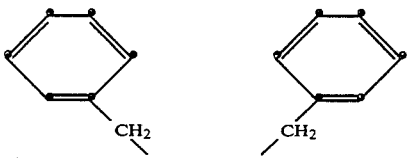 (9)

The preferred monomers have the structures:

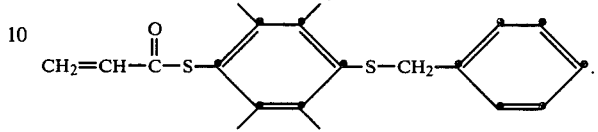 (1) (S—pentakis-(methylthio)-phenyl thioacrylate)

and

 (2) (S—pentakis-(methylthio)-phenyl thiomethacrylate).

The acrylate monomers are prepared by a method comprising (a) reacting a mercaptan with cuprous oxide to form a copper mercaptan and (b) reacting the resulting copper mercaptan with acryloyl chloride or methacryloyl chloride.

Thus, a method of preparing a monomer having the formula:

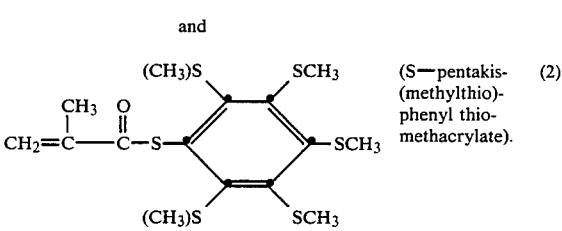

wherein $R^1$, $R^2$, $R^3$, $R^4$, $R^5$ and $R^6$ are as defined above comprises reacting a mercaptan having the formula:

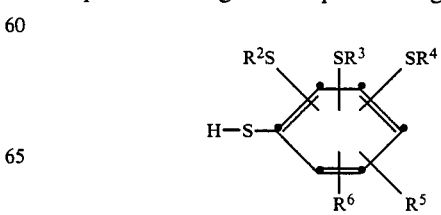

wherein $R^2$, $R^3$, $R^4$, $R^5$ and $R^6$ are as defined above with cuprous oxide and reacting the product of said reaction with acryloyl or methacryloyl chloride.

The product of the reaction of the above mercaptan with cuprous oxide is a composition of matter having the formula:

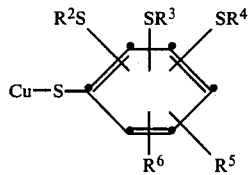

wherein $R^2$, $R^3$, $R^4$, $R^5$ and $R^6$ are as defined above.

Useful monomers which can be prepared using the novel method of this invention include S-pentakis(methylthio)phenyl thioacrylate, S-pentakis(methylthio)phenyl thiomethacrylate, S-(1-naphthylcarbinyl)thiomethacrylate, S-(1-naphthylcarbinyl)thioacrylate, S-benzylthioacrylate, S-benzylmethacrylate, and other acrylate or methacrylate monomers.

For example, S-pentakis(methylthio)phenyl thioacrylate is prepared by a method comprising reacting pentakis(methylthio)thiophenol with cuprous oxide and reacting the product of this reaction with acryloyl chloride.

The mercaptan starting material is prepared by methods known in the art. Such methods are described by Testaferri, Tingoli and Tieco, J.Org. Chem., 45, 4376 (1980), and Peach and Rayner, J. Fluorine Chem., 13, 447 (1979), the disclosures of which are hereby incorporated by reference.

The mercaptan is reacted with cuprous oxide preferably in a solvent such as dichloromethane or in acetonitrile with pyridine at reflux temperature and, conveniently, at about atmospheric pressure, over a period of 1 to 24 hours.

The product of this reaction is then reacted with acryloyl or methacryloyl chloride preferably in a solvent such as acetonitrile at reflux temperature and, conveniently, at about atmospheric pressure for a period of 1 to 24 hours.

The polymer of this invention is one having:

(a) from 5 to 100 mole percent of recurring units having the formula:

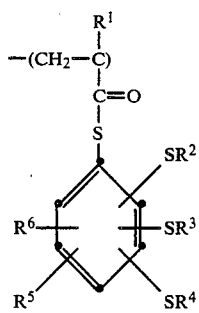

where $R^1$, $R^2$, $R^3$, $R^4$, $R^5$, and $R^6$ are described above; and (b) from 0 to 95 mole percent of a polymerized copolymerizable ethylenically unsaturated monomer.

Examples of copolymerizable ethylenically unsaturated monomers useful herein include alkyl acrylates and methacrylates such as methyl acrylate, ethyl acrylate, propyl acrylate, butyl acrylate, and butyl methacrylate; vinyl esters, amides, nitriles, ketones, halides, ethers, olefins and diolefins, as exemplified by acrylonitrile, methacrylonitrile, styrene, α-methyl styrene, acrylamide, methacrylamide, vinyl chloride, methyl vinyl ketone, fumaric, maleic and itaconic esters, 2-chloroethylvinyl ether, dimethylaminoethyl methacrylate, 2-hyroxyethyl methacrylate, N-vinylsuccinamide, N-vinylphthalimide, N-vinylpyrrolidone, butadiene, ethylene, and the thioacrylate monomers described in U.K. Patent Application GB No. 2093843 A.

Preferred monomers which are useful herein include acrylates and methacrylates. Especially preferred monomers include benzyl methacrylate and S-(1-naphthyl)methyl thioacrylate.

The novel polymer can be prepared by adding a small amount of photoinitiator (0.001–1.0 weight percent) such as benzoin methyl ether to the novel monomer or a mixture of preferably 5 to 100 mole percent of the novel monomer and 0–95% of a copolymerizable ethylenically unsaturated monomer described above. The mixture can be polymerized at a temperature of 20°–30° C. by irradiation with a near-ultraviolet lamp. The resulting polymer has an index of refraction above 1.70. The use of polymers having a refractive index over 1.70 in optical components permits the use of components which are considerably thinner than conventionally prepared components. Other methods of polymerization can similarly be used. Such methods can include thermal polymerization, polymerization by electron beam irradiation and polymerization by high energy gamma irradiation. Examples of the polymers of the invention include:

poly[S-pentakis(methylthio)phenyl thioacrylate]
poly[S-pentakis(methylthio)phenyl thiomethacrylate]
poly[S-pentakis(methylthio)phenyl thioacrylate-co-S-(1-naphthyl)methyl thioacrylate] .

The novel polymers of this invention are useful in optical components. The term "optical component" is defined as that portion of an optical assembly having as its function the refraction of light. As used herein, the term "optical component" is directed preferably toward components in which changes in refractive capability affect the overall utility of the component. "Refraction," as used herein, is defined as the deflection from a straight path undergone by a light ray or energy wave in passing obliquely from one medium (as air) into another (as glass or other optical material) in which its velocity is different. The term "optical assembly" as used herein is defined as a collection of manufactured parts in a complete machine, structure, or unit of a machine relating to the scientific study or use of electromagnetic radiation. The term "optical components" includes refractive materials, such as lenses, lens adhesives, prisms, mirrors, solid light pipes, light guides, fiber optics, phase-retardation plates and twistels, and in radiographic screens.

The term "prisms" as used herein is defined as a substantially transparent body bounded in part by two plane faces that are not parallel, said body being used to deviate or disperse a beam of light. Prisms can be used in telescopes, binoculars, beam splitters, rangefinders, spectroscopes, spectrographs, spectrophotometers, refractomers and anamorphic systems.

A "mirror" is defined as a polished or smooth surface (as glass) that forms images by reflection. Mirrors can be used in telescopes, beam splitters, rangefinders, reflecting microscope objectives and condensing systems.

A "solid light pipe" is defined as a substantially transparent body tapered to form a cone used to internally reflect a meridional ray incident on the untapered end of the cone from the conical wall at progressively lower angles of incidence until it is delivered to the tapered end of the cone, as described in Smith, *Modern Optical Engineering*, 1966, chapter 9. Light pipes can be used to enlarge the field of view of a radiometer with a small detector.

A "light guide" is defined as a substantially transparent body having substantially tubular pathways of higher-refractive index material encased by a lower-refractive index material used to internally reflect a meridional ray incident on the entrance end from the walls of the tubular pathways at substantially equal angles of incidence until it is delivered to the exit end of the guide, as described in U.S. Pat. No. 3,809,686. Light guides can be used in electronics to couple simple circuits optically and without capacitative effects.

"Fiber optics" are defined as substantially transparent bodies in the form of long polished cylinders in which light strikes the walls of the cylinder with an angle of incidence greater than the critical angle for total internal reflection used to transmit light from one end to another without substantial leakage, either as a single fiber or bound together in flexible bundles of fibers as disclosed by Smith, *Modern Optical Engineering*, 1966, chapter 9. Fiber optics are used in medical diagnostic instruments such as flexible gastroscopes, in fire detectors to relay signals to a sensor located behind a heat shield, in data-processing equipment to sense holes in punched cards or marks on examination forms, and in photometers and colorimeters to serve as flexible probes for a fixed sensor.

A "phase retardation plate" is defined as a substantially transparent body used to produce phase shifts in incident radiation resulting in elliptically or circularly polarized light. Phase retardation plates may be a pair of movable biaxial crystals in the form of wedges having perpendicularly aligned optical axes, such as Babinet compensators, Soleil compensators and the like. Or the desired phase shifts may be produced by total internal reflection in a phase retardation plate, such as a Fresnel rhomb. Various phase retardation plates are described by Kingslake, *Applied Optics and Optical Engineering*, 1965, volume I, chapter 9. Phase retardation plates are used in ellipsometers to study reflectance characteristics of metals and properties of surface films of liquids with polarized light.

In a particularly preferred embodiment of this invention, the monomers and polymers are useful as materials for making lenses. A "lens" is a substantially transparent body having two opposite regular surfaces, either both curved or one curved and the other plane, and which is used either singly or combined in an optical instrument for forming an image by focusing rays of light. It has been found that, because of the higher refractive index of these polymers, it is possible to produce lenses which are thinner than lenses made with polymers having refractive indices under 1.70, e.g., polymethylmethacrylate, n=1.49 to 1.50.

The lenses of this invention are not only thinner than conventionally prepared lenses, but require less curvature, occupy a smaller volume of space and thus provide more freedom in assembly of multi-element lenses than prior art lenses. They also require less polymer to produce, constituting a potential cost savings to the manufacturer.

In another preferred embodiment of this invention, the monomers and polymers are useful as materials for making radiographic intensifying screens comprising a phosphor in a polymeric binder. U.S. Pat. No. 3,023,313 issued Feb. 27, 1962 to DeLaMater et al discloses x-ray intensifying screens with improved speed having a polymeric binder with a refractive index as close to that of an alkali metal halide phosphor as possible. However, because of substantial differences between the refractive index of selected binders and the refractive index of the phosphor, reflecting pigments must be added.

Monomers of this invention are useful in producing optical components by polymerization in situ. Thus, the resulting polymer forms the final material of which the optical component is comprised.

In a preferred embodiment, a lens is prepared from the novel polymer in the following manner. A mixture of from 5 to 100 mole percent of a preferred monomer, such as from 0 to 95 mole percent of a copolymerizable ethylenically unsaturated monomer, such as S-(1-naphthyl)methyl thioacrylate, and a small amount of photoinitiator is prepared. A preferred molar ratio for the mixture is about 1:5 S-pentakis(methylthio)phenyl thioacrylate:S-(1-naphthyl)methyl thioacrylate. A mold of the desired shape, such as a concave glass lens is filled with the mixture and covered with a sheet of plate glass. The assembly is polymerized by irradiation of near-ultraviolet light. The resulting lens is clear and transparent and contains the polymer of this invention having a refractive index over 1.70.

The following examples are included for a further understanding of the invention.

EXAMPLE 1

(a) Preparation of Pentakis(methylthio)thiophenol

The reaction is conducted in a two-liter round bottomed flask equipped with a thermometer and a magnetic stir bar under an atmosphere of nitrogen. Five hundred ml dry N,N-dimethylformamide (reagent grade) having a melting point of −60° C. is added. The flask and its contents are cooled by an external dry ice/acetone cooling bath until the measured temperature of the solvent is −20° C. or less. Extreme cooling such that freezing of the solvent occurs is avoided. Vials nominally containing 50 g (1.04 mole; 8.5 equivalents) of methanethiol having a boiling point of +6° C. are cooled to reduce the internal pressure; the sealed glass vials are opened, and the contents are added directly to the precooled N,N-dimethylformamide without additional weighing. In this manner most of the extremely volatile thiol is transferred successfully. The mixture is stirred for 15 minutes. Next, 48 g of a 50% dispersion of sodium hydride in oil (available from Alfa Venton, catalogue number 35106), containing 24 g NaH, 1.00 mole, 8.16 equivalents) is added portionwise with vigorous stirring, over a period of 30 minutes, such that a temperature rise is avoided. Next, a slurry of 34.9 g (0.12 mole) hexachlorobenzene in 200 ml N,N-dimethylformamide having a boiling point of 153° C. is added to the cooled solution of sodium methanethiolate in N,N-dimethylformamide. Stirring is continued for 15 minutes. The cooling bath is removed and the reaction mixture is allowed to warm to room temperature. Then the flask and its contents are heated in an oil bath until the solvent refluxes; refluxing is continued for 30 minutes. The flask is cooled to room temperature; the contents are poured into 700 ml of water. This mixture is extracted with ether (saving the aqueous phase). The ether extract is washed with water (saving the aqueous phase) and with 5% aqueous sodium hydroxide solution. All of the aqueous phases containing sodium pentakis(methylthio)thiophenolate are combined, neutralized with dilute aqueous hydrochloric acid, and extracted several times with ether. The combined etheral phases are washed with a saturated aqueous sodium chloride solution, dried with anhydrous sodium sulfate, and filtered. The ether solution is boiled to remove residual volatile components (methanethiol reactant and dimethyl sulfide by-product), and then evaporated on a rotary evaporator, yielding a residue of 38–40 g crude product (91–96% yield).

The crude pentakis(methylthio)thiophenol is redissolved in ether; pentane is added to the point of cloudiness, the mixture is decolorized with carbon, filtered, and recrystallized from pentane/ether solution. Two or three recrystallizations provide a pale yellow solid. The melting point is 95.5–97°. Roughly half of the weight of the crude material is routinely obtained as pure material; additional pure material is more tediously obtained from the combined mother liquors.

(b) Preparation of Cuprous Pentakis(methylthio)thiophenolate

To a solution of 10.0 g (29.4 mmol) of pentakis(methylthio)thiophenol in 200 ml dichloromethane (reagent grade) is added 2.5 g (17.5 mmol; 19% excess) cuprous oxide. The mixture is heated to reflux (55°–60° C.) under a nitrogen atmosphere for 16 hours.

Next, the mixture is cooled to room temperature and filtered, removing a small amount of solid presumed to be excessed cuprous oxide.

The solvent is removed from the filtrate on a rotary evaporator; the solid residue is rinsed with acetonitrile and ether (removing small amounts of soluble material) and air-dried, providing 11.3 g (95.5%) of dark iridescent solid.

(c) Preparation of S-Pentakis(methylthio)phenyl Thioacrylate

A mixture of 5.4 g (0.13 mmol) cuprous pentakis(methylthio)thiophenolate in 250 ml dry acetonitrile with 1.3 ml (0.13 mmol) acryloyl chloride is refluxed gently (90°–95°) for 2.5–3.0 hours in a nitrogen atmosphere, with stirring. After this time, a dark solution is present with a minimal amount of undissolved solid. The mixture is cooled to room temperature and poured into 500 ml ether. The ether solution is washed with saturated aqueous sodium bicarbonate; at this point insoluble material precipitates which is filtered off and set aside. The clear ether filtrate is washed again with saturated aqueous sodium bicarbonate solution, with water, and with saturated aqueous sodium chloride solution, dried with anhydrous magnesium sulfate, filtered, and evaporated. The semi-solid residue remaining is dissolved in dichloromethane. The dichloromethane solution is diluted four-fold with heptane (to the point of cloudiness), decolorized with carbon, filtered, and evaporated, yielding 4.65 g (88%) clear yellow oil. The infrared spectrum clearly indicates a clean $\alpha,\beta$-unsaturated thioester (C=O stretch 1675 cm$^{-1}$; C=C stretch 1605 cm$^{-1}$) with no saturated ester impurities (1740 cm$^{-1}$).

An attempt was made to record the refractive index of a sample of this monomer with a simple Abbe refractometer. The refractometer reading with this sample was off-scale, indicating a refractive index of greater than 1.71.

EXAMPLE 2

Polymer from S-Pentakis(methylthio)phenyl Thioacrylate 0.25 gram of the somewhat yellow sample of monomer from Example 1 was copolymerized in bulk with 1.25 grams of S-(1-naphthyl)methyl thioacrylate by placing the mixture of monomers, containing a small amount of photoinitiator between two glass plates and irradiating with 366 nm ultraviolet light.

A sample of monomer in ether solution was polymerized and spontaneously precipitated a nearly white solid, soluble in dichloromethane, with chromatographic behavior typical of a polymer.

EXAMPLE 3

Preparation of S-(1-Naphthylcarbinyl) Thiomethacrylate

Into a 1000-ml round-bottomed flask equipped with a mechanical stirring rod, reflux condenser, and nitrogen inlet were added 15.0 g (86 mmol) of 1-naphthylcarbinyl mercaptan, 5.4 g (38 mmol) pulverized cuprous oxide and 450 ml acetonitrile. Then 13.53 g (171 mmol) pyridine were added. With vigorous stirring, the mixture was heated to reflux (approx. 95°–100° C.) for 20 hours under a nitrogen atmosphere. The mixture was cooled to room temperature and filtered. The filter cake was rinsed with acetonitrile and with ether and air dried to provide 16.4 g (92% yield) of copper (I) 1-naphthylcarbinyl mercaptide. The product was a tan or yellow solid, insoluble in all common solvents.

Combustion analysis (N, C, H, S) and neutron activation analysis (Cu) of this material agree satisfactorily with the expected value. This yellowish product contained discrete red lumps which comprise approximately 30% of the sample by weight; analyses of the red lumps indicates that they were composed of approximately 3% cuprous oxide and 97% copper (I) 1-naphthylcarbinyl mercaptide. Thus overall the product contained approximately 1% unreacted cuprous oxide.

Into a 500-ml round-bottomed flask fitted with a nitrogen inlet and magnetic stir bar were added 5.0 g (211 mmol) copper (I) 1-naphthylcarbinyl mercaptide, 2.6 g (253 mmol; 20% excess) methacryloyl chloride and 250 ml acetonitrile. The reaction was stirred for 20 hours under a nitrogen atmosphere at room temperature. The mixture was filtered to remove insoluble cuprous chloride; the filtrate was evaporated to a small volume, and the residue was dissolved in ether, with filtration to remove insoluble material. The ethereal solution was washed with water, with saturated aqueous sodium bicarbonate solution, and with saturated aqueous sodium chloride solution. The ethereal solution was dried over anhydrous magnesium sulfate and evaporated to provide 5.36 g (104%) of S-(1-naphthylcarbinyl)thiomethacrylate, identified by its $^1$H=nmr spectrum.

EXAMPLE 4

Preparation of S-(1-Naphthylcarbinyl) Thioacrylate

Reaction of copper (I) 1-naphthylcarbinyl mercaptide with acryloyl chloride, similar to Example 3, provided the thioacrylate in 95.4% yield.

The invention has been described in detail with particular reference to certain preferred embodiments thereof, but it will be understood that variations and modifications can be effected within the spirit and scope of the invention.

What is claimed is:

1. A monomer having the formula:

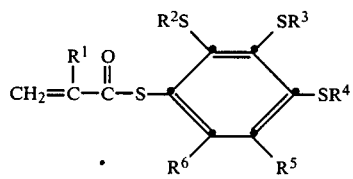

wherein:
$R^1$ is H or methyl;
$R^2$, $R^3$ and $R^4$ are alkyl; and
$R^5$ and $R^6$ are thioalkyl.

2. The monomer of claim 1 wherein $R^2$, $R^3$, $R^4$, $R^5$ and $R^6$ each contain from 1 to 6 carbon atoms.

3. A monomer having the formula:

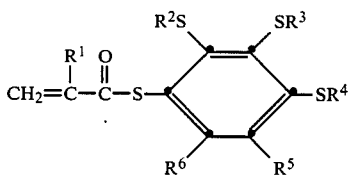

wherein:
$R^1$ is H or methyl;
$R^2$, $R^3$ and $R^4$ are alkyl; and
$R^5$ and $R^6$ are thioalkyl, with the proviso that $SR^2$, $SR^3$, $SR^4$, $R^5$ and $R^6$ represent the same group.

4. The monomer of claim 3 wherein $R^2$, $R^3$, $R^4$, $R^5$ and $R^6$ each contain from 1 to 6 carbon atoms.

5. A monomer having the formula:

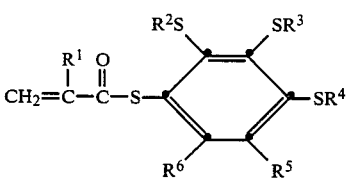

wherein:
$R^1$ is H or methyl;
$R^2$, $R^3$ and $R^4$ are aryl; and
$R^5$ and $R^6$ are thioaryl.

6. The monomer of claim 5 wherein $R^2$, $R^3$ and $R^4$ are phenyl or naphthyl and $R^5$ and $R^6$ are thiophenyl or thionaphthyl.

7. A monomer having the formula:

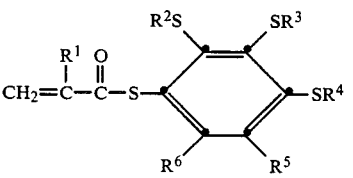

wherein:
$R^1$ is H or methyl;
$R^2$, $R^3$ and $R^4$ are aryl; and
$R^5$ and $R^6$ are thioaryl, with the proviso that $SR^2$, $SR^3$, $SR^4$, $R^5$ and $R^6$ represent the same group.

8. The monomer of claim 7 wherein $R^2$, $R^3$ and $R^4$ are phenyl or naphthyl and $R^5$ and $R^6$ are thiophenyl or thionaphthyl.

9. A monomer having the formula:

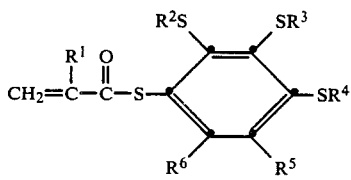

wherein:
$R^1$ is H or methyl;
$R^2$, $R^3$ and $R^4$ are aralkyl; and
$R^5$ and $R^6$ are thioaralkyl.

10. The monomer of claim 9 wherein $R^2$, $R^3$ and $R^4$ are benzyl and $R^5$ and $R^6$ are thiobenzyl.

11. A monomer selected from the group consisting of

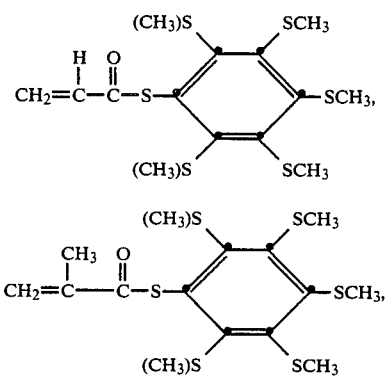

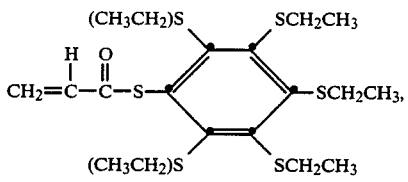

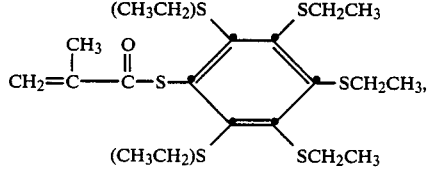

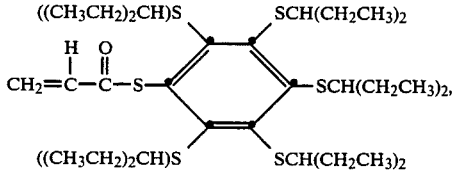

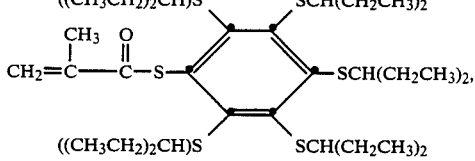

-continued
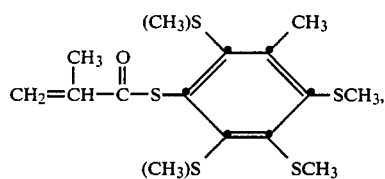
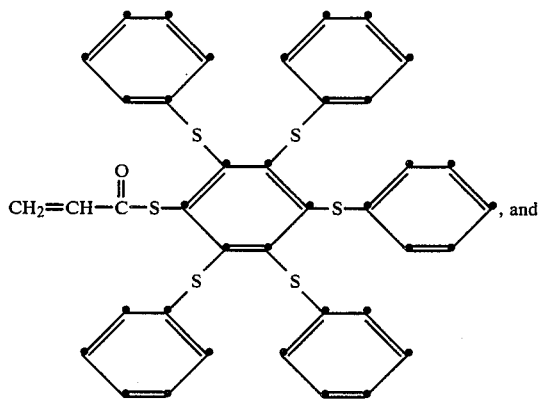, and
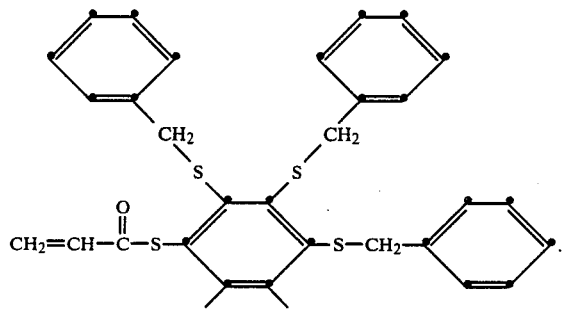
12. A monomer having the formula:
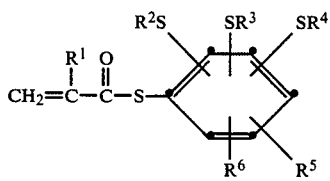
wherein:
R$^1$ is H or methyl;
R$^2$, R$^3$ and R$^4$ are methyl; and
R$^5$ and R$^6$ are thiomethyl.
13. The monomer of claim 12 having the formula:
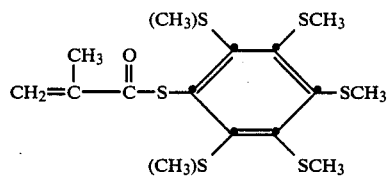
14. The monomer of claim 12 having the formula:
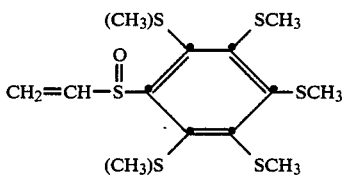
* * * * *